United States Patent
Freiberg et al.

(10) Patent No.: US 6,270,501 B1
(45) Date of Patent: Aug. 7, 2001

(54) SURGICAL METHOD AND APPARATUS AND CANNULATED SCALPEL FOR USE THEREIN

(75) Inventors: Andrew A. Freiberg; Steven A. Goldstein, both of Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/435,560

(22) Filed: Nov. 8, 1999

(51) Int. Cl.⁷ .................................................. A61B 17/32
(52) U.S. Cl. ................................................................ 606/79
(58) Field of Search ........................... 606/79, 80, 82, 606/83, 87, 88, 89, 96, 104, 166, 170, 181, 183, 81, 86, 167; 433/72, 74, 75, 76, 165, 166; 30/289

(56) References Cited

U.S. PATENT DOCUMENTS

| | | | |
|---|---|---|---|
| 878,524 | * | 2/1908 | Gregory ............................ 30/123.3 |
| 3,583,390 | * | 6/1971 | Jascalevich ........................... 606/170 |
| 3,659,607 | * | 5/1972 | Banko ................................... 606/170 |
| 3,719,186 | | 3/1973 | Merig, Jr. . |
| 4,769,018 | | 9/1988 | Wilson . |
| 4,787,378 | * | 11/1988 | Sodhi ..................................... 606/79 |
| 4,927,421 | | 5/1990 | Goble et al. . |
| 5,129,901 | | 7/1992 | Decoste . |
| 5,190,548 | * | 3/1993 | Davis ..................................... 606/80 |
| 5,201,733 | | 4/1993 | Etheredge, III . |
| 5,203,784 | * | 4/1993 | Ross et al. ........................... 606/104 |
| 5,234,435 | | 8/1993 | Seagrave, Jr. . |
| 5,458,604 | | 10/1995 | Schmieding . |
| 5,571,127 | | 11/1996 | DeCampli . |
| 5,611,801 | | 3/1997 | Songer . |
| 5,690,677 | | 11/1997 | Schmieding et al. . |
| 5,697,944 | * | 12/1997 | Lary ..................................... 606/170 |
| 5,697,947 | | 12/1997 | Wolf et al. . |
| 5,718,706 | * | 2/1998 | Roger ................................... 606/104 |
| 5,795,323 | | 8/1998 | Cucin . |
| 5,855,579 | | 1/1999 | James et al. . |
| 5,893,862 | | 4/1999 | Pratt et al. . |
| 5,897,560 | * | 4/1999 | Johnson ................................. 606/86 |

\* cited by examiner

*Primary Examiner*—Jeffrey A. Smith
*Assistant Examiner*—Eduardo C. Robert
(74) *Attorney, Agent, or Firm*—Brooks & Kushman P.C.

(57) ABSTRACT

A surgical method and apparatus and cannulated scalpel for use therein are provided. In particular, the cannulated scalpel is used during surgical procedures to make an incision through intervening tissue about a guide pin having an end for engaging a target tissue, such as bone. The scalpel includes a hollow, elongated shaft adapted to slide over the guide pin and a head mounted at one end of the shaft. The head has at least one leading cutting edge that is adapted to cut along a plane through the intervening tissue as the shaft slides over the guide pin toward the target tissue engaging end of the guide pin. The scalpel can then be removed from the incision along the plane, preferably with the aid of a trailing guide edge. Following removal of the scalpel, a driving tool, such as a power surgical drill, can be introduced to drive a cannulated fastener along the guide pin and through the incision to embed the fastener in the target tissue and provide fixation of the target tissue.

26 Claims, 4 Drawing Sheets

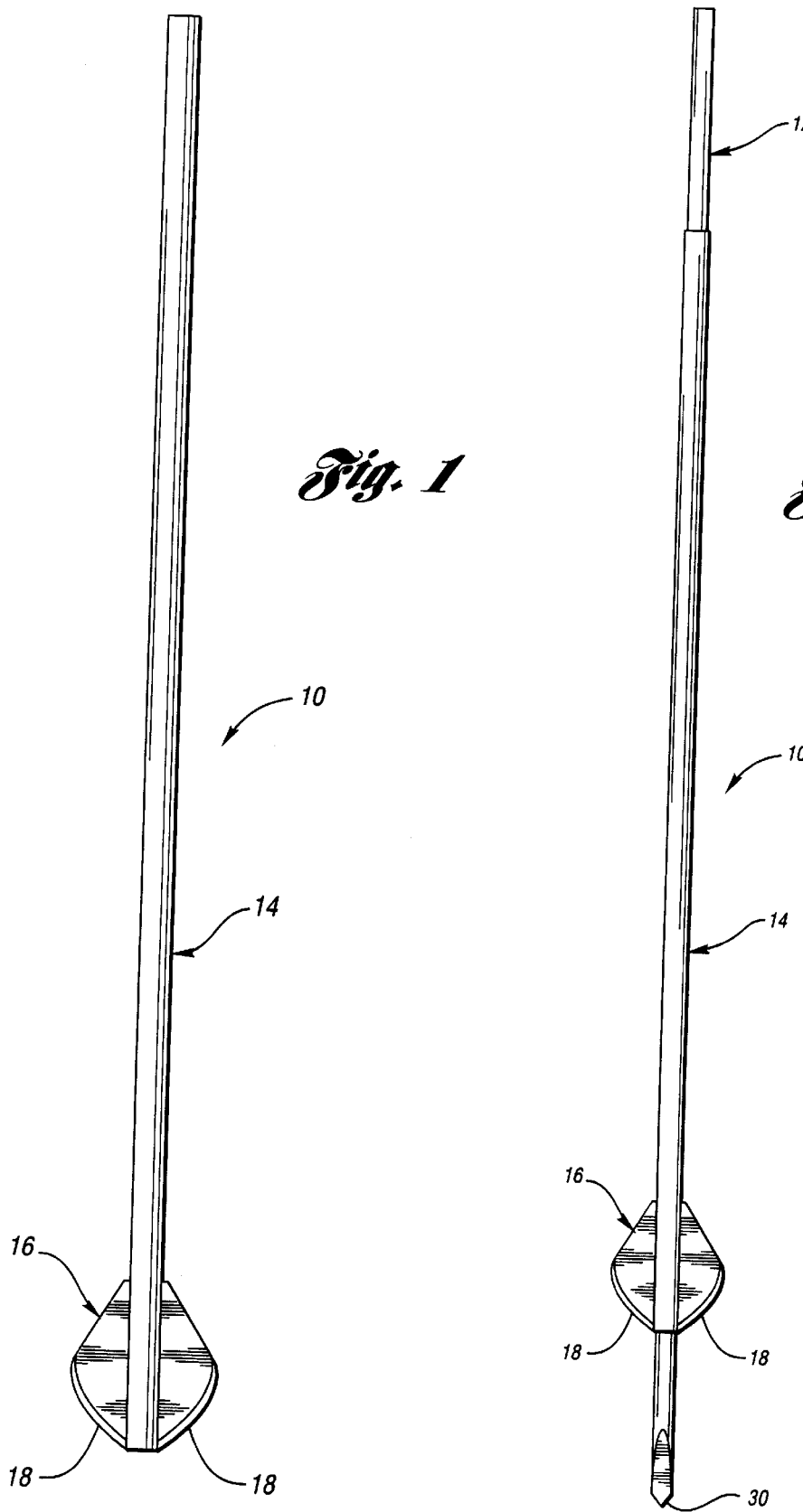

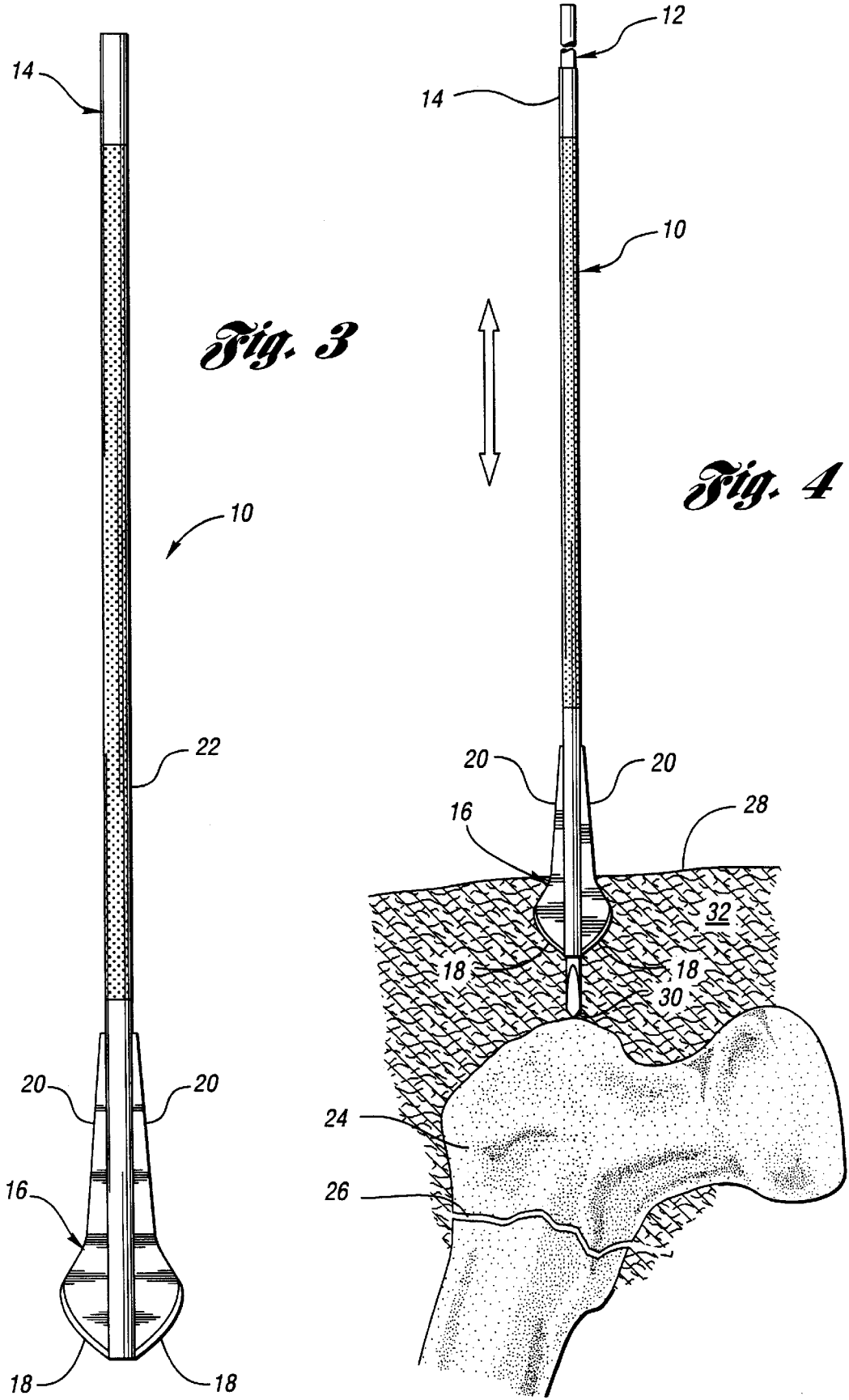

SURGICAL METHOD AND APPARATUS AND CANNULATED SCALPEL FOR USE THEREIN

TECHNICAL FIELD

This invention relates to a surgical method and apparatus and cannulated scalpel for use therein.

BACKGROUND ART

Bone fractures are a relatively common injury requiring orthopaedic care. While some fractures can be treated through reduction and immobilization, certain types of bone fractures cannot be effectively healed without fixation, typically utilizing bone screws or fixation pins. The placement of pins or screws is typically accomplished by inserting a guide pin through the skin and into contact with the bone surface. Then, a power surgical drill or reamer is used to clear tissue and drive a fixation device, such as a cannulated bone screw or pin, over the guide pin and into the bone across the fracture area.

Prior to driving the fixation device into place, the tissue surrounding the guide pin should be loosened to allow for passage of the cannulated screw or pin through to the bone. At present, this is accomplished by cutting around the guide pin with a conventional scalpel. However, using a standard scalpel to cut precisely around the guide pin is difficult and time consuming due the small circumference of the guide pin and the depth that the bone may lie from the skin surface. As a result, the soft tissue surrounding the pin typically undergoes unnecessary damage, which only prolongs its healing process. In addition, the cosmetic result of such imprecise cuts is not desirable for the patient.

DISCLOSURE OF INVENTION

Therefore, it is an object of the present invention to provide a surgical method and apparatus and cannulated scalpel for use therein that results in a more precise, efficient incision through tissue during surgical procedures.

Accordingly, a cannulated scalpel is provided for use in surgical procedures, wherein the scalpel is used to make an incision through intervening tissue about a guide pin having an end for engaging a target tissue, such as bone. The scalpel includes a hollow, elongated shaft adapted to slide over the guide pin and a head mounted at one end of the shaft. The head has at least one leading cutting edge that is adapted to cut along a plane through the intervening tissue as the shaft slides over the guide pin toward the target tissue engaging end of the guide pin.

Preferably, the head has a trailing guide edge to facilitate removal of the scalpel from the incision along the plane. The trailing guide edge can also be adapted to cut along the plane through the intervening tissue. In a preferred embodiment, the head has a pair of spaced leading cutting edges adapted to cut along a pair of planes through the tissue. With this embodiment, a pair of spaced trailing guide edges can be provided to facilitate removal of the scalpel from the incision along the pair of planes.

Correspondingly, a method for making an incision about a guide pin is provided, where the guide pin has a target tissue engaging end that is engaged with a target tissue. The method includes sliding a cannulated scalpel over the guide pin toward the target tissue engaging end of the guide pin in order to cut along a plane through the intervening tissue, wherein the cannulated scalpel has a hollow, elongated shaft and a head mounted at one end of the shaft, the head having at least one cutting edge.

In addition, an apparatus for providing fixation of a target tissue, such as bone, is provided. The apparatus includes a guide pin having a target tissue engaging end and a cannulated scalpel for making an incision through intervening tissue about the guide pin. The scalpel has a hollow, elongated shaft adapted to slide over the guide pin and a head mounted at one end of the shaft. The head has at least one leading cutting edge adapted to cut along a plane through the intervening tissue as the shaft slides over the guide pin toward the target tissue engaging end of the guide pin. The apparatus further includes a driving tool, such as a power surgical drill, for driving a cannulated fastener along the guide pin and through the incision to embed the fastener in the target tissue and provide fixation of the target tissue.

Correspondingly, a method for providing fixation of a target tissue is provided. The method includes inserting a guide pin having a target tissue engaging end through intervening tissue and into engagement with the target tissue, such as bone. The method further includes sliding a cannulated scalpel over the guide pin toward the target tissue engaging end of the guide pin in order to make an incision through the intervening tissue about the guide pin. The cannulated scalpel has a hollow, elongated shaft and a head mounted at one end of the shaft, wherein the head has at least one leading cutting edge for cutting along a plane through the intervening tissue. Next, the method includes removing the cannulated scalpel from the incision along the plane, preferably using a trailing guide edge to facilitate removal. Lastly, the method includes driving a cannulated fastener along the guide pin and through the incision to embed the fastener in the target tissue and provide fixation of the target tissue.

The above object and other objects, features, and advantages of the present invention are more readily understood from a review of the attached drawings and the accompanying specification and claims.

BRIEF DESCRIPTION OF DRAWINGS

FIG. 1 is a perspective view of the cannulated scalpel of the present invention;

FIG. 2 is a perspective view of the cannulated scalpel of FIG. 1 engaged with a conventional surgical guide pin;

FIG. 3 is a perspective view of a preferred embodiment of the cannulated scalpel of FIG. 1;

FIG. 4 is a perspective view of the cannulated scalpel with a guide pin during fracture fixation;

BEST MODE FOR CARRYING OUT THE INVENTION

Figure 5:
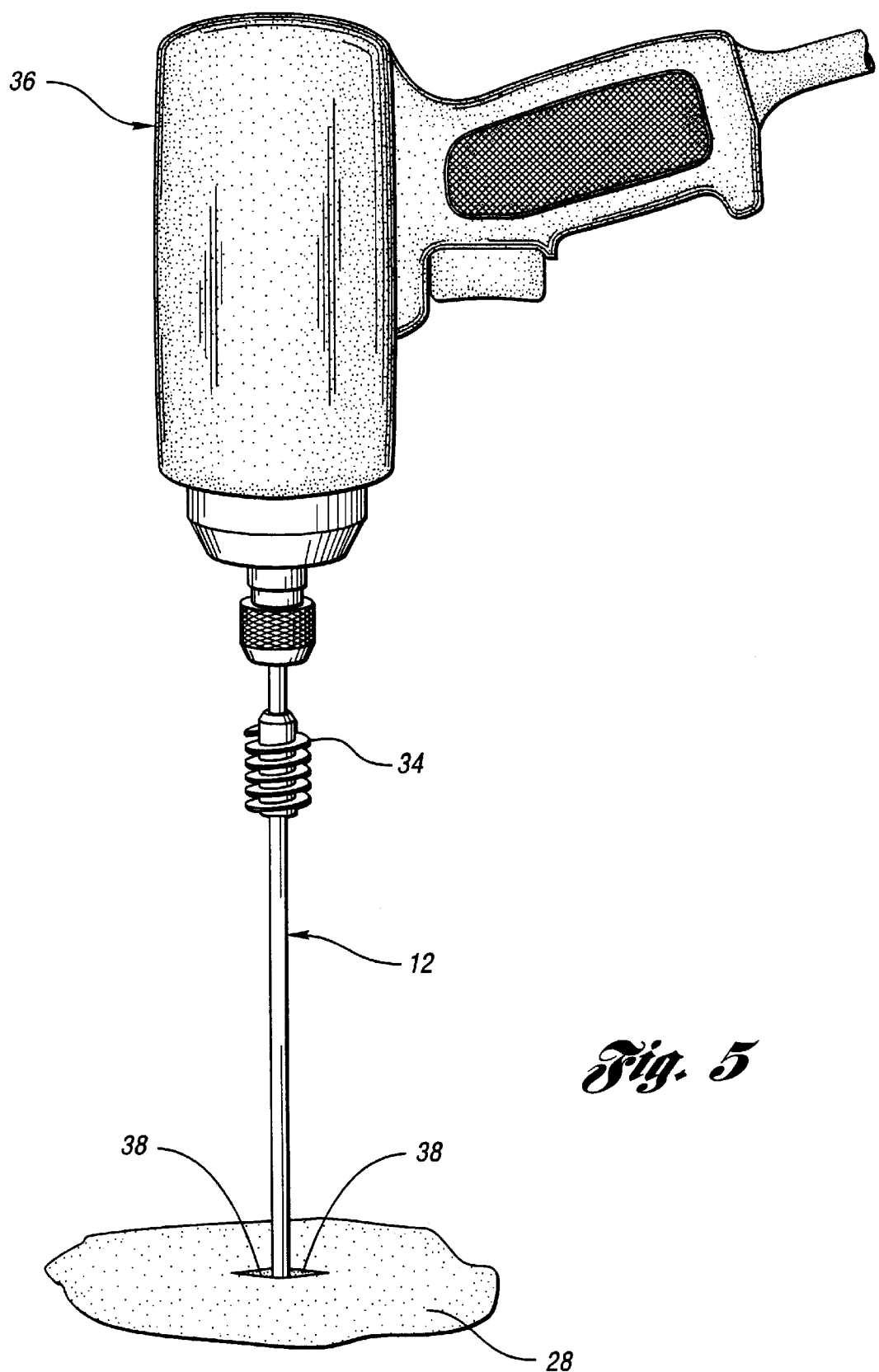
FIG. 5 is a perspective view, partially broken away, illustrating the surgical elements necessary for fracture fixation after removal of the cannulated scalpel.

Referring first to FIG. 1, a cannulated scalpel, designated by reference numeral 10, is shown constructed in accordance with the present invention. Cannulated scalpel 10 can be used during an surgical procedure, such as fracture fixation, where an incision is required through soft tissue. In particular, cannulated scalpel 10 is designed to slide over a guide pin 12, as shown in FIG. 2. Guide pin 12 is inserted through a patient's skin and into engagement with a target tissue, such as bone.

As shown in FIG. 1, cannulated scalpel 10 comprises a hollow, elongated shaft 14 adapted to slide over guide pin 12. Cannulated scalpel 10 further comprises a head 16 mounted at one end of shaft 14. Head 16 may be integrally formed with shaft 14 or affixed thereto by welding or the like. Head 16 has at least one leading cutting edge 18 adapted to cut along a plane through intervening tissue between the skin and target tissue as shaft 14 slides over guide pin 12. In the embodiment depicted in FIG. 1, head 16 has a pair of spaced leading cutting edges 18 adapted to cut along a pair of planes through the intervening tissue. Of course, any number of leading cutting edges 18 can be employed with cannulated scalpel 10 of the present invention. Likewise, the length and width of leading cutting edge 18 is entirely variable, typically depending on the size of the incision necessary for clear access of surgical tools to the target tissue.

Shaft 14 of cannulated scalpel 10 can be of any length appropriate for the intended surgical procedure. For example, a cannulated scalpel for pediatric use. Shaft 14 can be constructed from any suitable material such as metal or plastic. Entire cannulated scalpel 10 can be disposed of after use, or can be reused as long as its materials of construction are suitable for sterilization. Alternatively, shaft 14 can be designed to be reusable and head 16 attached to shaft 14 in such as way as to be removable and replaceable, similar to a conventional scalpel.

When the target tissue is located at a great depth beneath the skin's surface, leading cutting edges 18 of cannulated scalpel 10 will no longer be visible to an operator once formation of the incision down to the target tissue is achieved. Since it is desirable to removed cannulated scalpel 10 along the same plane in which it was inserted to avoid unnecessary tissue damage, it is advantageous to have a visual indicator for the operator that cannulated scalpel 10 is being removed in alignment with the plane previously cut. Therefore, in a preferred embodiment shown in FIG. 3, head 16 includes at least one trailing guide edge 20 to facilitate removal of cannulated scalpel 10 from the incision along the plane. In the embodiment shown, head 16 has a pair of spaced trailing guide edges 20 to facilitate removal of cannulated scalpel 10 from the incision along the pair of planes created by spaced leading edges 18. In addition to serving their alignment function, trailing guide edges 20 can also be adapted to cut along the plane through the intervening tissue. As with leading cutting edges 18 described above, the number, length, and width of trailing guide edges 20 is entirely variable, and is typically dependent on the parameters of corresponding leading cutting edges 18.

In addition to or in place of trailing guide edges 20, shaft 14 and guide pin 12 could be provided with indicators (not shown) formed thereon which can be aligned to facilitate insertion and removal of cannulated scalpel 10 along a chosen plane. Similarly, mating mechanical protrusions and indentations (not shown) could be provided on shaft 14 and guide pin 12 to aid in alignment. Still further, markings (not shown) could be provided on shaft 14 of cannulated scalpel 10 to indicate its depth of insertion into the tissue. As shown in FIG. 3, shaft 14 preferably includes an exterior grip surface 22 to provide additional control for an operator during use.

Referring next to FIG. 4, guide pin 12 and cannulated scalpel 10 are shown during the initial stages of a making an incision, such as for fracture fixation. In the example shown, the target tissue 24 comprises bone, and a fracture 26 is present therein. In order to provide fixation of fracture 26, guide pin 12 is inserted through a patient's skin 28 and into contact with target tissue 24. Typically, guide pin 12 is provided with a specialized end 30 for engaging target tissue 24. Once guide pin 12 is positioned, an operator slides the cannulated scalpel over guide pin 12 toward its target tissue engaging end 30 in order to cut along a plane through the intervening tissue 32 with leading cutting edges 18. After the operator is satisfied with the depth of the incision, cannulated scalpel 10 can be removed by sliding scalpel 10 along guide pin 12 in the opposite direction. Preferably, cannulated scalpel 10 is removed along the plane formed by leading cutting edges 18, preferably using trailing guide edges 20 to facilitate alignment. After removal of cannulated scalpel 10, a retractor (not shown) can be used to keep the tissue spread apart for surgical tools to follow.

During a fracture fixation procedure, guide pin 12 is left in engagement with target tissue 24 in order to provide a path along which a cannulated fastener, such as a cannulated pin or the standard cannulated screw 34 shown, can be delivered for fracture repair, as depicted in FIG. 5. Cannulated screw 34 can be constructed of any material that is suitable for implantation into target tissue 24, and may even be biodegradable. A driving tool, such as a power surgical drill 36, is operable to drive cannulated screw 34 along guide pin 12, through the incision 38 formed by leading cutting edges 18, and across fracture 26 to provide fixation thereof. Such surgical power drills are known in the art, and typically include a driver which is cannulated to travel along guide pin 12 and fit into cannulated screw 34. Alternatively, cannulated screw 34 can be manually driven into target tissue 24, such as with a cannulated screwdriver (not shown). Once cannulated screw 34 is secured in target tissue 24, guide pin 12 can be removed.

Figure 6:
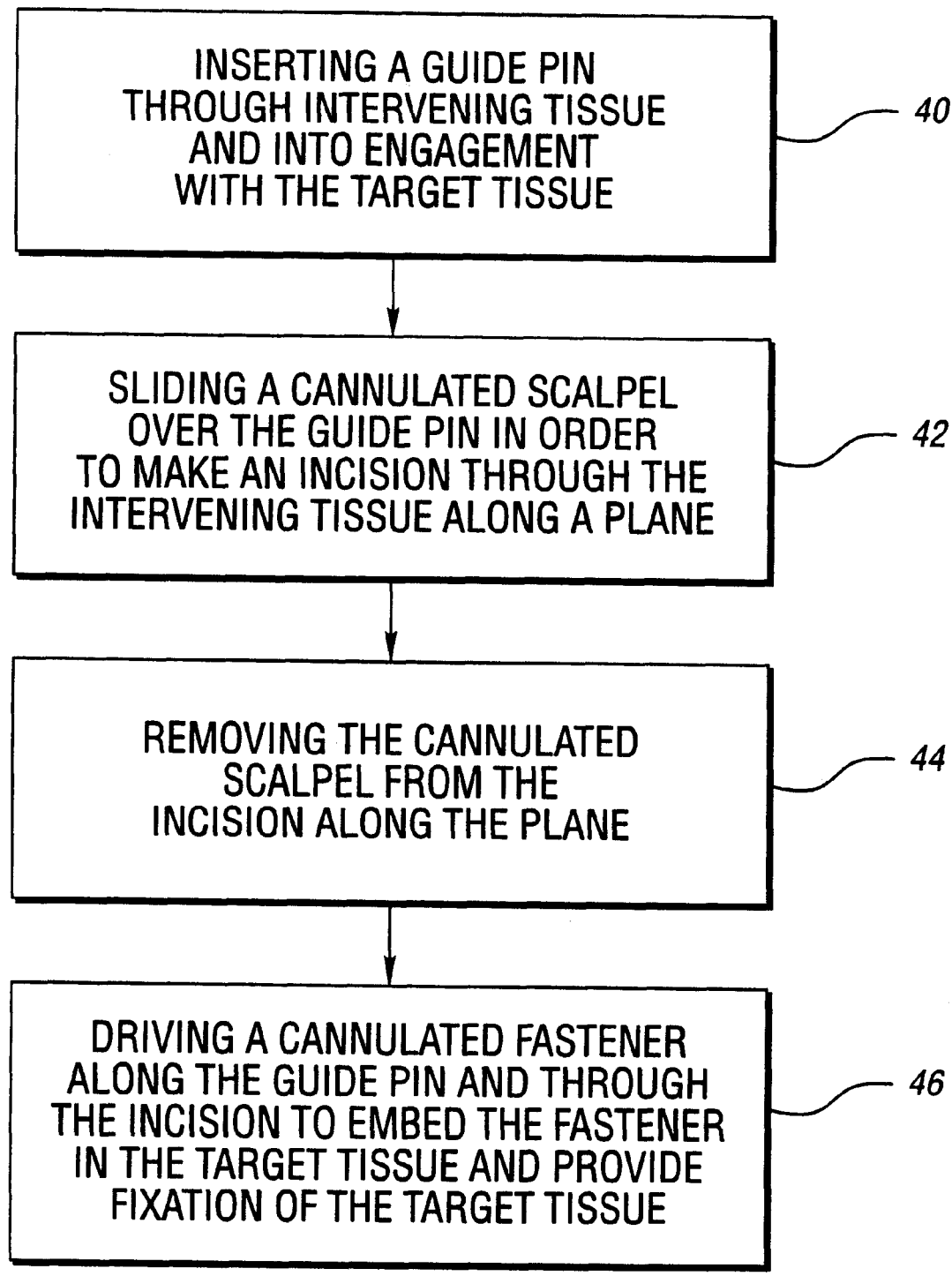
FIG. 6 is a block diagram flow chart of a preferred method of fracture fixation in accordance with the present invention.

Referring now to FIG. 6, a corresponding preferred method for providing fixation of a target tissue is outlined. As shown at block 40, the method includes inserting a guide pin having a target tissue engaging end through intervening tissue and into engagement with the target tissue. The method further includes sliding a cannulated scalpel over the guide pin toward the target tissue engaging end of the guide pin in order to make an incision through the intervening tissue along a plane, as shown at block 42. Next, as shown at block 44, the method includes removing the cannulated scalpel from the incision along the plane. Lastly, as shown at block 46, the method includes driving a cannulated fastener along the guide pin and through the incision to embed the fastener in the target tissue and provide fixation of the target tissue.

Although cannulated scalpel 10 and the method for its use have been described herein in the context of bone fracture fixation, it should be understood that cannulated scalpel 10 can be utilized for any surgical procedure where clean access through soft tissue is desired. For example, cannulated scalpel 10 of the present invention can be used in hip and knee joint surgery, spinal operations, cartilage repair, ligament fixation, biopsies, and various sports medicine applications. Furthermore, cannulated scalpel 10 could be configured to be connected to auxiliary equipment, such as an electrocautery device, for expanded functionality.

While embodiments of the invention have been illustrated and described, it is not intended that these embodiments illustrate and describe all possible forms of the invention. Rather, the words used are words of description rather than limitation, and it is understood that various changes may be made without departing from the spirit and scope of the invention.

What is claimed is:

1. A cannulated scalpel for making an incision through intervening tissue about a guide pin having a target tissue engaging end, the scalpel comprising:

a hollow, elongated shaft having first and second ends, the first and second ends including openings which allow the shaft to slide over the guide pin;

a head mounted adjacent the second end of the shaft, the head having at least one leading cutting edge projecting outwardly beyond the width of the shaft and adapted to cut along a plane through the intervening tissue as the shaft slides over the guide pin toward the target tissue engaging end of the guide pin.

2. The scalpel of claim 1, wherein the head has a trailing guide edge to facilitate removal of the scalpel from the incision along the plane.

3. The scalpel of claim 2, wherein the trailing guide edge is adapted to cut along the plane through the intervening tissue.

4. The scalpel of claim 1, wherein the head has a pair of spaced leading cutting edges adapted to cut along a pair of planes through the tissue.

5. The scalpel of claim 4, wherein the head has a pair of spaced trailing guide edges to facilitate removal of the scalpel from the incision along the pair of planes.

6. The scalpel of claim 1, wherein the shaft includes an exterior grip surface.

7. The scalpel of claim 1, wherein the scalpel is disposable.

8. The scalpel of claim 1, wherein the head is disposable.

9. The scalpel of claim 1, wherein the shaft is constructed of metal.

10. The scalpel of claim 1, wherein the shaft is constructed of plastic.

11. A method for making an incision through intervening tissue about a guide pin, the guide pin having a target tissue engaging end that is engaged with a target tissue, the method comprising:

sliding a cannulated scalpel over the guide pin toward the target tissue engaging end of the guide pin, the cannulated scalpel comprising a hollow, elongated shaft having first and second ends, the first and second ends including openings, and a head mounted adjacent the second end of the shaft, the head having at least one leading cutting edge projecting outwardly beyond the width of the shaft, in order to cut along a plane through the intervening tissue.

12. The method of claim 11, further comprising removing the scalpel from the incision along the plane using a trailing guide edge.

13. The method of claim 12, wherein removing the scalpel from the incision using a trailing guide edge includes cutting along the plane with the trailing guide edge.

14. An apparatus for providing fixation of a target tissue, the apparatus comprising:

a guide pin having a target tissue engaging end;

a cannulated scalpel for making an incision through intervening tissue about the guide pin, the scalpel comprising a hollow, elongated shaft having first and second ends, the first and second ends including openings which allow the shaft to slide over the guide pin, and a head mounted adjacent the second end of the shaft, the head having at least one leading cutting edge projecting outwardly beyond the width of the shaft and adapted to cut along a plane through the intervening tissue as the shaft slides over the guide pin toward the target tissue engaging end of the guide pin; and a driving tool for driving a cannulated fastener along the guide pin and through the incision to embed the fastener in the target tissue and provide fixation of the target tissue.

15. The apparatus of claim 14, wherein the driving tool is operable to embed the fastener in bone.

16. The apparatus of claim 14, wherein the head has a trailing guide edge to facilitate removal of the scalpel from the incision along the plane.

17. The scalpel of claim 16, wherein the trailing guide edge is adapted to cut along the plane through the intervening tissue.

18. The scalpel of claim 14, wherein the head has a pair of spaced leading cutting edges adapted to cut along a pair of planes through the tissue.

19. The scalpel of claim 18, wherein the head has a pair of spaced trailing guide edges to facilitate removal of the scalpel from the incision along the pair of planes.

20. The apparatus of claim 14, wherein the driving tool is a power surgical drill.

21. The apparatus of claim 14, wherein the cannulated fastener comprises a cannulated screw.

22. The apparatus of claim 14, wherein the cannulated fastener comprises a cannulated pin.

23. A method for providing fixation of a target tissue, the method comprising:

inserting a guide pin having a target tissue engaging end through intervening tissue and into engagement with the target tissue;

sliding a cannulated scalpel over the guide pin toward the target tissue engaging end of the guide pin in order to make an incision through the intervening tissue about the guide pin, the cannulated scalpel comprising a hollow, elongated shaft and a head mounted at one end of the shaft, the head having at least one leading cutting edge for cutting along a plane through the intervening tissue;

removing the cannulated scalpel from the incision along the plane; and driving a cannulated fastener along the guide pin and through the incision to embed the fastener in the target tissue and provide fixation of the target tissue.

24. The method of claim 23, wherein driving the cannulated fastener includes embedding the fastener in bone.

25. The method of claim 23, wherein removing the scalpel includes removing the scalpel along the plane using a trailing guide edge.

26. The method of claim 25, wherein removing the scalpel along the plane using a trailing guide edge includes cutting along the plane with the trailing guide edge.

* * * * *